United States Patent [19]

Bruce et al.

[11] Patent Number: 5,217,496
[45] Date of Patent: Jun. 8, 1993

[54] IMPLANT AND METHOD OF MAKING IT

[75] Inventors: Lars Bruce; Ingrid Bruce, both of Viken, Sweden

[73] Assignee: AB Idea, Sweden

[21] Appl. No.: 953,770

[22] Filed: Sep. 30, 1992

Related U.S. Application Data

[63] Continuation of Ser. No. 613,907, Dec. 10, 1990, abandoned.

[30] Foreign Application Priority Data

Jun. 14, 1988 [SE] Sweden ............................ 8802214

[51] Int. Cl.⁵ .............................................. A61F 2/28
[52] U.S. Cl. ........................................ 623/16; 623/18; 433/169
[58] Field of Search .................... 623/16, 18, 20, 66; 433/169

[56] References Cited

U.S. PATENT DOCUMENTS

| | | | |
|---|---|---|---|
| 3,605,123 | 9/1971 | Hahn | 623/16 |
| 3,905,047 | 9/1975 | Long | 623/16 |
| 3,918,100 | 11/1975 | Shaw et al. | 3/1.9 |
| 4,505,266 | 3/1985 | Yannas et al. | 128/1 R |
| 4,539,716 | 9/1985 | Bell | 623/12 |
| 4,936,852 | 6/1990 | Kent et al. | 623/18 |
| 5,002,488 | 3/1991 | Homsy | 433/169 |

FOREIGN PATENT DOCUMENTS

WO87/06842 11/1987 World Int. Prop. O. .

OTHER PUBLICATIONS

Surgery, Mar. 1986, Sentissi, J. M. et al., "The effect of Flow on Vescular Endothelial Cells Grown in Tissue Culture on Polytetrafluoroethylene Grafts", vol. 99 (3), pp. 337-343.

Surgery, May 1987, Anderson, J. S. et al., "In Vitro Endothelialization of Small-Caliber Vesouler Grafts", vol. 101 (5), pp. 577-586.

Primary Examiner—Randall L. Green
Assistant Examiner—Gina M. Gualtier
Attorney, Agent, or Firm—Bacon & Thomas

[57] ABSTRACT

An implant (prosthesis) comprises biological material in its surface intended to face the body tissue. The surface is formed of a layer (3) consisting of a mixture of grains (5) of tissue-compatible type and disintegrated tissue-compatible biological material (4).

In a method of making the implant, an implant body (2) and a mixture of grains (5) of tissue-compatible type and disintegrated tissue-compatible biological material (4) as well as a nutrient solution (6) for the latter are placed in a mould (8). The biological material is allowed to grow in the mould, both out to the boundary wall of the mould cavity and in to the implant body.

12 Claims, 1 Drawing Sheet

IMPLANT AND METHOD OF MAKING IT

This application is a continuation of application Ser. No. 07/613,907, filed Dec. 10, 1990 now abandoned.

BACKGROUND OF THE INVENTION

1. Field of the Invention

The present invention relates to an implant and a method of making it.

2. Discussion of Related Art

Implants consisting of or having a surface layer of tissue-compatible material, such as titanium and certain types of ceramic materials, are already known, e.g. from SE-7902035-0.

A common feature of most of these implants is that they are designed for closely engaging the biological tissue, such that this rapidly contacts and grows into the implant. To this end, femoral prostheses, for example, are often formed with projections by means of which the prosthesis catches onto the inner wall of the femoral cavity.

This, however, results in an unresilient joint between the surface of the implant and the opposing body tissue, which is a disadvantage, especially in the case of spongy tissues, such as in jaws.

Despite the provision of projections, the healing process will take quite a long time, which not only causes discomfort to the patient but may also give rise to the formation of connective tissue in the joint between the implant and the tissue.

The object of the present invention is to overcome, or at least substantially reduce the above-mentioned drawbacks in prior-art implants.

SUMMARY OF THE INVENTION

According to the invention, this object is achieved in that the implant in its surface intended to face the body tissue, comprises tissue-compatible biological material, preferably tissue, and most preferably endogenous tissue of the same type as that in which or against which the implant should be inserted or placed, respectively.

The surface of the implant is formed of a layer provided on a supporting body or anchoring elements (the term "supporting body" as used hereinafter should also be considered to include "anchoring elements") consisting of or having a surface layer of tissue-compatible material, said layer comprising a mixture of grains/pulverulent material of tissue-compatible type and disintegrated tissue-compatible biological material which has grown, both out to the outer surface of the implant and into the supporting body, and by the latter growth has been linked to the supporting body, said growth of the biological material also generally linking the pulverulent particles/grains to each other. To promote such growth, use is made of a suitable commercially available nutrient solution.

The supporting body or its surface layer is advantageously of titanium, and its outer surface is advantageously porous for optimum tissue anchorage.

The tissue-compatible grains can be selected from different materials, primarily titanium, but other materials known to those skilled in the art can be used, such as bioceramics, bioglass and hydroxyapatite.

It will be appreciated that the implant according to the invention, containing biological material in its surface layer, will reduce the time required for healing after implantation, i.e. the time required for biological anchorage of the implant in or against body tissue.

The implant according to the invention is advantageously made in a mould, the cavity of which contains the supporting body (or the part thereof to be provided with said layer) and a mixture of said material in the space between the supporting body and the boundary wall of the mould cavity. To this mixture contained in the mould cavity is added a nutrient solution promoting (optionally after replenishment) the growth of the biological material in the mixture. The growth parameters are available in the literature to those skilled in the art.

One advantage of such a technique is that the implant can easily be tailor-made for the patient. The mould cavity is provisionally shaped after e.g. a dental bed, and any modifications of the implant that may later be required are determined by radiography after implantation of the implant shaped in the mould. Modifications of the mould cavity are then performed for obtaining a more correct implant.

DETAILED DESCRIPTION OF PREFERRED EMBODIMENTS

Figure 1:
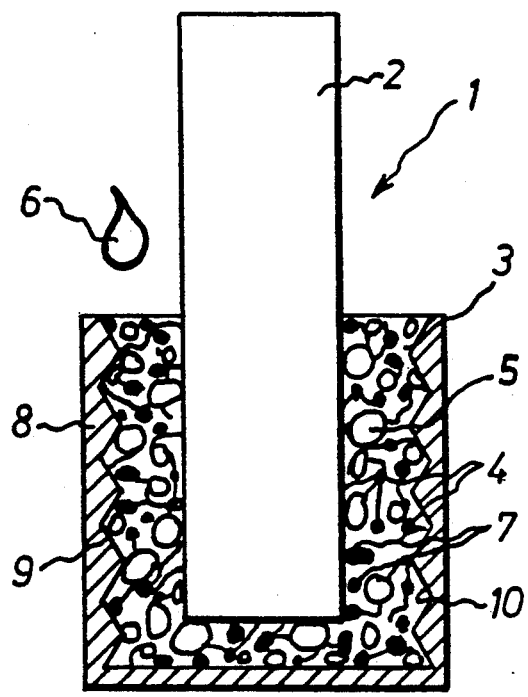
FIGS. 1 and 2 illustrate two embodiments of the invention.

FIG. 1 shows a dental prosthesis 1 to be screwed into a jaw. The supporting body 2 of the prosthesis is of tissue-growth promoting titanium having a porous outer surface (obtained by sintering, metal deposition by vaporisation etc.). To the supporting body, is fixed a layer 3 consisting of a mixture of ground living bone tissue 4 ground from jawbone tissue taken from the patient, and titanium powder (i.e., disjointed particles) 5. The mixture has been supplied with a nutrient solution 6 causing the ground living bone tissue in the mixture to grow and form tissue 7 linking the components 4, 5 of the layer 3 to each other and to the surface of the supporting body 2. The prosthesis has been made in a silicon mould 8 with threads 9 on its inner side, thus forming threads 10 on the outer surface of the dental prosthesis.

Figure 2:
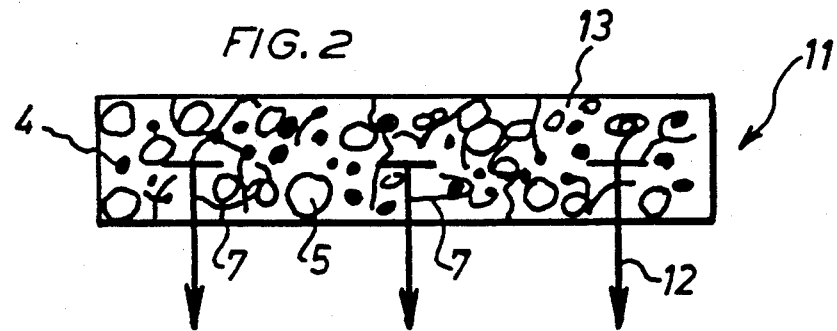

FIG. 2 shows a cartilaginous implant 11 provided with several titanium pins 12 having porous surfaces similar to supporting body 2 embedded with one end in a layer 13 of the mixture described above. With the opposite, free ends of the pins 12, the implant 11 can be fixed to body tissue.

We claim:

1. An implant suitable for use in living tissue comprising:
    a support body having a porous outer surface and a surface layer on said support body outer surface, said surface layer having an outer surface and comprising biocompatible material, including a mixture of disjointed granulated tissue compatible material and disintegrated living biological tissue material, said disintegrated living biological tissue material grown in a nutrient to form a biological tissue material that extends both to the outer surface of said surface layer and into the outer surface of the supporting body so as to be linked thereto, said grown biological tissue material linking together said disjointed granulated tissue compatible material.

2. An implant according to claim 1 wherein the support body comprises titanium.

3. An implant according to claim 1, wherein the granulated tissue compatible material comprises titanium.

4. An implant according to claim 1, wherein the disintegrated living biological tissue material is tissue similar to tissue at a location of the implant.

5. An implant suitable for use in living tissue comprising:
- a body of biocompatible material, having an outer surface, and at least one anchoring element having a portion embedded in said material and a portion extending away from said material, said imbedded portion having a porous outer surface;
- said biocompatible material comprising a mixture of disjointed granulated tissue compatible material and disintegrated living biological tissue material, said disintegrated living biological tissue material grown in a nutrient to form a biological tissue material that extends to the outer surface of said body of tissue compatible material and into the outer surface of the embedded portion of the anchoring element so as to be linked thereto, said grown biological tissue material linking together said disjointed granulated tissue compatible material.

6. An implant according to claim 5, wherein said embedded portion comprises titanium.

7. An implant according to claim 5, wherein the granulated tissue compatible material comprises titanium.

8. An implant according to claim 5, wherein the disintegrated living biological tissue material is tissue similar to tissue at a location of the implant.

9. An implant suitable for use in living bone tissue comprising:
- a support body comprising titanium having a porous outer surface and a surface layer on said support body outer surface, said surface layer having an outer surface and comprising biocompatible material, including a mixture of disjointed granulated tissue compatible material and disintegrated living biological tissue material, said disintegrated living biological tissue material grown in a nutrient to form a biological tissue material that extends both to the outer surface of said surface layer and into the outer surface of the supporting body so as to be linked thereto, said grown biological tissue material linking together said disjointed granulated tissue compatible material;
- said disjointed granulated tissue compatible material comprising titanium particles;
- said disintegrated living biological tissue material comprising disintegrated living bone tissue.

10. An implant suitable for use in living body tissue comprising:
- a body of biocompatible material, having an outer surface and at least one anchoring element having a portion embedded in said biocompatible material and a portion extending away from said biocompatible material;
- said biocompatible material comprising a mixture of disjointed granulated tissue compatible material and disintegrated living biological tissue material, said disintegrated living biological tissue material grown in a nutrient to form a biological tissue material that extends to the outer surface of said body of tissue compatible material and into the embedded portion of the anchoring element so as to be linked thereto, said grown biological tissue material linking together said granulated tissue compatible material with said grown biological tissue material;
- said disjointed granulated tissue compatible material comprising titanium particles;
- said disintegrated living biological tissue material comprising disintegrated living bone tissue;
- said embedded portion of said anchoring element comprising titanium having a porous surface into which the biological tissue material has grown.

11. A method of making an implant body comprising:
- placing a supporting body having a porous outer surface and mixture of disjointed granular tissue compatible material and disintegrated living biological tissue material as well as a nutrient solution for the latter in a mold cavity, said mold cavity having a boundary wall, said supporting body being smaller than the mold cavity, and allowing the biological tissue material to grow both out to the boundary wall of the mold cavity and into the supporting body while linking together the disjointed granular tissue compatible material; and
- removing the implant body and mixture from the mold cavity.

12. A method of making an implant body comprising:
- placing at least a portion of an anchoring element having a porous outer surface and a mixture of disjointed granular tissue compatible material and disintegrated living biological tissue material as well as a nutrient solution for the latter in a mold cavity, said mold cavity having a boundary wall said anchoring element portion being smaller than the mold cavity, and allowing the biological tissue material to grow both out to the boundary wall of the mold cavity and into the portion of the anchoring element while linking together the disjointed granular tissue compatible material; and removing the anchoring element and mixture from the mold.

* * * * *